United States Patent [19]

Woo

[11] 3,959,334

[45] May 25, 1976

[54] LIME SOAP DISPERSANT COMPOUNDS

[75] Inventor: Gar Lok Woo, Tiburon, Calif.

[73] Assignee: Chevron Research Company, San Francisco, Calif.

[22] Filed: July 31, 1972

[21] Appl. No.: 276,637

Related U.S. Application Data

[63] Continuation of Ser. No. 790,470, Jan. 10, 1969, abandoned.

[52] U.S. Cl. .............................. 260/459 R; 252/121; 252/550; 260/457; 260/458; 260/635 D
[51] Int. Cl.² ................ C07C 141/08; C07C 141/10
[58] Field of Search ................ 260/459 R, 458, 457

[56] References Cited
UNITED STATES PATENTS

| | | | |
|---|---|---|---|
| 1,942,812 | 1/1934 | Guenther et al. | 260/459 R |
| 1,968,793 | 7/1934 | Bertsch | 260/459 R |
| 1,968,795 | 7/1934 | Bertsch | 260/459 R |
| 2,014,782 | 9/1935 | Schrauth et al. | 260/459 R |
| 2,618,649 | 11/1952 | Van Bavel et al. | 260/459 R |

*Primary Examiner*—Norman Morgenstern
*Attorney, Agent, or Firm*—G. F. Magdeburger; John Stoner, Jr.

[57] ABSTRACT

New compositions of matter useful as lime soap dispersants comprise the 2-hydrocarbyl-1,4-butanediol disulfates.

4 Claims, No Drawings

LIME SOAP DISPERSANT COMPOUNDS

This is a continuation of application Ser. No. 790,470 filed 1-10-69, now abandoned.

BACKGROUND OF THE INVENTION

The present invention is concerned with the field of lime soap formation and precipitation, and more particularly with novel 2-hydrocarbyl-1,4-butanediol disulfates suitable as lime soap dispersants.

It is well known that the use of ordinary toilet soaps in hard water gives rise to the formation and precipitation of insoluble fatty acid salts, commonly referred to as "lime soaps." These precipitated lime soaps tend to coagulate and form a sticky curd, which is especially noticeable in washstands, bathtubs, and the like, where it rises to the surface of the water and adheres around the tub or wash basin as a ring. In laundry applications, the scum or curd affects the laundry tub in a like manner but, in addition, adheres to the clothes. As a result, the clothes take on a grey, dingy appearance, develop spots upon ironing, and often a rancid odor. Similarly, when used for washing the hair, lime soaps are deposited thereon, giving the hair a coarse feeling and a dull appearance.

It has now been found that lime soap formation and precipitation can be substantially avoided by incorporating in the soap, e.g., a tallow soap, a minor but effective amount of a watersoluble 2-hydrocarbyl-1,4-butanediol disulfate.

SUMMARY OF THE INVENTION

Novel 2-hydrocarbyl-1,4-butanediol disulfate compounds are excellent lime soap dispersants. These compounds may be represented by the formula:

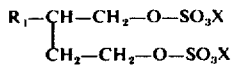

wherein X is hydrogen or a water-soluble, salt-forming cation and $R_1$ is a hydrocarbyl radical containing from 14 – 36 carbon atoms. $R_1$ may be represented by the formula:

wherein $R_2$ and $R_3$ are hydrogen or saturated or unsaturated, straight-chain or branched-chain hydrocarbyl radicals containing from 0 – 35 carbon atoms. In a preferred embodiment, the hydrocarbyl radical $R_1$ is a saturated or unsaturated straight-chain group containing from 14 – 24 carbon atoms.

The hydrocarbyl-1,4-butanediol disulfates as described within the scope of the present invention may be prepared by the hydride reduction and catalytic hydrogenation of alkenyl succinic anhydrides to produce either alkenyl or alkyl diols, respectively, and subsequent sulfation of the diols. The alkenyl succinic anhydrides may be produced by the condensation of maleic anhydride with an olefin.

By an alternative method, the alkenyl succinic anhydride may be reacted with an alcohol to produce the diester and then reduced to the alkyl butanediol. By controlled reduction, unsaturated portions in the alkenyl chain may be preserved.

The novel 2-hydrocarbyl-1,4-butanedioldisulfates of the present invention may be prepared by sulfating 2-hydrocarbyl-1,4-butanediols where the hydrocarbyl radical may be alkyl or alkenyl selected from, but not limited to, the following: tetradecyl, pentadecyl, hexadecyl, heptadecyl, octadecyl, nonadecyl, eicosyl, heneicosyl, docosyl, tricosyl, tetracosyl, pentacosyl, hexacosyl, heptacosyl, octacosyl, nonacosyl, triacontyl, hentriacontyl, dotriacontyl, tritriacontyl, tetratriacontyl, pentatriacontyl, hexatriacontyl, tetradecenyl, pentadecenyl, hexadecenyl, heptadecenyl, octadecenyl, nonadecenyl, eicosenyl, heneicosenyl, docosenyl, tricosenyl, tetracosenyl, pentacosenyl, hexacosenyl, heptacosenyl, octacosenyl, nonacosenyl, tricontenyl, hentriacontenyl, dotriacontenyl, tritriacontenyl, tetratriacontenyl, pentatriacontenyl, and hexatriacontenyl.

The diols may be converted to disulfates by sulfation with chlorosulfonic acid, $SO_3$, oleum and other known sulfating agents. The sulfated product may be neutralized with aqueous basic solutions containing compounds such as hydroxide, carbonates, and oxides of the alkali metals, alkaline earth metals and ammonium and other water-soluble, salt-forming cationic agents. The cationic portion may also be formed from a low molecular weight tertiary amine, such as triethanol amine.

The particular soap which can be used in accordance with the present invention is not critical. Any of the watersoluble soaps in bar form normally used in industrial, laundering, and toilet applications are contemplated. As is known, these soaps can be prepared from a variety of fatty and oily materials, such as tallow, coconut oil, cottonseed oil, corn oil, soybean oil, olive oil, palm oil, lard greases, fish oils, and the like. The cation portion of the soap is so selected as to impart sufficient hardness to the soap to form a bar. Thus, the cation can be sodium, potassium, or nitrogen-containing, such as the ammonium soaps or those derived from triethanol amine. In general, water-soluble sodium salts of fatty acids derived from tallow and coconut oil are preferred because of the ease with which they can by formed into a bar.

In addition, synthetic detergents may also be incorporated into the soap bars with no adverse effect on the lime soap dispersants. Such detergents include, but are not limited to, the water-soluble salts of alkylbenzenesulfonates, linear alkylbenzenesulfonates, alkyl sulfonates, alkyl sulfates, olefin sulfonates, and hydrogenated olefin sulfonates, the cationic portion being as noted above.

The method of addition of the additive of the present invention is not critical. It thus can be added to the crutcher after the soap has been made by saponification of fats. Or the additive can be added to soap chips and detergent in an amalgamator, if desired, along with other soap additives conventionally used, such as coloring agents, perfume, fillers, and the like.

The following examples describe the preparation of the lime soap dispersant compounds of the present invention.

EXAMPLE 1

Preparation of Alkylbutanediol disulfate from Alkyl Succinic Anhydride 13.3 g. of lithium aluminum hydride was added slowly with stirring to a 2-liter, 3-necked flask containing 250 ml. of diethyl ether. 81 g. of n-hexadecyl succinic anhydride was dissolved in 1,000 ml. of ethyl ether and slowly added to the flask. The mixture was heated up until refluxing began and continued for a total of 33 hours with intermittent interruptions when the mixture was allowed to stand overnight and over the weekend. After heating for 16 ½ hours, 3.0 g. of additional lithium aluminum hydride was added. After 33 hours of reaction time, infrared analysis indicated the absence of carbonyl groups.

Ethyl acetate, 20 ml., was added to the reaction mixture to consume the remaining lithium aluminum hydride and the mixture was transferred to a 4-liter erlenmeyer flask containing 300 ml. of ice and 72 g. of concentrated HCl. The mixture was stirred with a magnetic stirrer and an additional 72 g., 10 g. at a time, of HCl was added. The mixture was transferred to a separatory funnel. After shaking and separating the layers, the aqueous phase was extracted with 200 ml. of ether. The combined ether extracts were washed with 150 ml. of water and twice with 100 ml. portions of saturated sodium bicarbonate solution. The solution was dried over anhydrous magnesium sulfate and filtered to remove the magnesium sulfate. From the residue of 67 g., 61 g. of 2-n-hexadecyl-1,4-butanediol (84.0 per cent yield) was recovered by vacuum distillation at less than 0.6 mm. of pressure for approximately 3 hours.

EXAMPLE 2

Preparation of Alkenylbutanediol from Alkenyl Succinic Anhydride

The general procedure of Example 1 was followed, except that 189 g. (0.5 mole) of n-eicosenyl succinic anhydride and a total charge of 34 g. of lithium aluminum hydride were substituted as reactants. The final residue gave 110 g., 60 per cent yield, of 2-n-eicosenyl-1,4-butanediol.

EXAMPLE 3

Sulfation of 2-n-hexadecyl-1,4-butanediol

A 300 ml., 3-necked, round bottom flask was charged with 18.9 g. (0.06 mole) of 2-n-hexadecyl-1,4-butanediol and 50 ml. of dry methylene chloride. After cooling the mixture to 10°C., a solution of 15.45 g. of chlorosulfonic acid in 10 ml. of methylene chloride was added slowly over a period of approximately 20 minutes. The temperature was maintained at about 10°C. Stirring was continued for an additional 10 minutes. The reaction mixture was then transferred to a dropping funnel. The flask was charged with 6.4 g. of sodium hydroxide dissolved in a mixture of 25 ml. of water and 75 ml. of ethanol and cooled to 5°–10°C. The acid solution was then added dropwise, keeping the temperature below 10°C. After 30 minutes' additional stirring, the pH was 8–9. Sodium bicarbonate (0.2 g.) and ethanol (100 ml.) were added and the mixture was heated to remove methylene chloride. Temperature was maintained at 55°C. for 3/4 of an hour. The precipitated salt was removed by hot suction filtration, and the filtrate cooled and 100 ml. of water added. De-oiling was accomplished by extraction with four 75 ml. portions of n-pentane (total oil extracted equalled 1.02 g.). The solvent was evaporated from the aqueous phase, and there was obtained 32.5 g. of 2-n-hexadecyl-1,4-butanediol disulfate disodium salt. The product was recrystallized twice with methanol and dried in a vacuum oven.

EXAMPLE 4

Sulfation of 2-n-eicosenyl-1,4-butanediol

Substantially the same procedure of Example 3 was followed, except that 22.1 g. (0.06 mole) of 2-n-eicosenyl-1,4-butanediol and 9 ml. (0.135 mole) of chlorosulfonic acid were used. 21.8 g. of 2-n-eicosenyl-1,4-butanediol disulfate, disodium salt was obtained.

The mixtures of the present invention will generally comprise, in weight per cent based on soap, synthetic detergent when present, and lime soap dispersant, of from 30 to 99, and preferably from 50 to 95 per cent soap; from 0 to 69, and preferably 0 to 50 per cent synthetic detergent; and from 1 to 50, and preferably 5 to 10 per cent lime soap dispersant.

In evaluating a satisfactory lime soap dispersant, a good method and the one used in the examples hereinbelow appearing is as follows: A stock solution of the test dispersant is prepared by dissolving 1 part by weight of the dispersant in 99 parts of distilled water. Stock solutions of the tallow soap are also prepared again the concentration of the organic material in the solution being 1 per cent by weight.

Since the stock solutions are made up to the same concentration, the relative amount of each solution determines the relative per cents of tallow soap and dispersant for each test. For example, a follows: Place per cent dispersant test is carried out as follows:Place 1 ml. of the dispersant solution and 9 ml. of the tallow-soap-containing solution in the bottom of a 100 ml. stopper graduate cylinder and swirl it gently. When well mixed, dilute with 90 ml. of 334 parts per million hard water (2 parts calcium to 1 part magnesium, calculated as carbonates) at 110°F. The final hardness is 300 ppm. The graduate is then shaken vigorously for 15 seconds, and then allowed to stand for 5 minutes. At the end of this time, the milliliters of curd are measured and recorded.

The following tabulated examples illustrate the practice of the invention:

TABLE I

| Examples | Hydrocarbyl Radical | Concentration Dispersant | Concentration Tallow Soap | Curd (Ml.) | Disodium Disulfate Sulfur Analysis Calculated | Disodium Disulfate Sulfur Analysis Found |
|---|---|---|---|---|---|---|
| 5 | — | 0 | 100 | 5 | — | — |
| 6 | decyl | 5 | 95 | 2 | — | — |
| 7 | ″ | 10 | 90 | 2 | — | — |
| 8 | dodecyl | 5 | 95 | 1 | 13.85 | 13.5 |
| 9 | ″ | 10 | 90 | 2 | — | — |
| 10 | tetradecyl | 5 | 95 | 2 | — | — |
| 11 | ″ | 10 | 90 | 0 | — | — |
| 12 | hexadecyl | 5 | 95 | 0 | 12.35 | 12.3 |
| 13 | ″ | 10 | 90 | 0 | — | — |
| 14 | octadecyl | 5 | 95 | 0 | 11.71 | 11.5 |
| 15 | ″ | 10 | 90 | 0 | — | — |
| 16 | mixture of n-$C_{18-20}$ unsaturated | 5 | 95 | 0 | 11.40 | 11.1 |

TABLE I-continued

| Examples | Hydrocarbyl Radical | Concentration Dispersant | Tallow Soap | Curd (Ml.) | Disodium Disulfate Sulfur Analysis Calculated | Found |
|---|---|---|---|---|---|---|
| 17 | '' | 10 | 90 | 0 | — | — |
| 18 | eicosenyl | 5 | 95 | 0 | 11.19 | 10.9 |
| 19 | '' | 10 | 90 | 0 | — | — |
| 20 | docosenyl | 5 | 95 | 0 | 10.66 | 9.75 |
| 21 | '' | 10 | 90 | 0 | — | — |

As is evidenced from the data in Table I, essentially no curd is formed when the hydrocarbyl butanediol dissulfate lime soap disperant contains at least 14 carbon atoms in the hydrocarbyl radical.

What is claimed is:

1. The compounds of the formula:

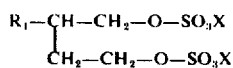

wherein X is hydrogen or a water-soluble, salt-forming cation and $R_1$ is a hydrocarbyl radical containing from 14 to 36 carbon atoms and represented by the formula:

wherein $R_2$ and $R_3$ are hydrogen, alkyl or alkenyl radicals containing from 0 – 35 carbon atoms.

2. A compound as in claim 1, wherein X is selected from the group consisting of sodium, potassium, ammonium, magnesium, calcium and triethanol amine.

3. A compound as in claim 2, wherein $R_1$ is selected from the group consisting of n-hexadecyl, n-octadecyl, n-nonadecyl, n-eicosyl, and n-docosyl.

4. A compound as in claim 2, wherein $R_2$ and $R_3$ are independently selected from the group consisting of saturated straight-chain, unsaturated straight-chain, saturated branched-chain, unsaturated branched-chain, and hydrogen.

* * * * *